(12) United States Patent
Schneider et al.

(10) Patent No.: US 6,964,720 B2
(45) Date of Patent: Nov. 15, 2005

(54) ELASTOMERIC NONWOVEN LAMINATES AND PROCESS FOR PRODUCING SAME

(75) Inventors: Uwe Schneider, Mason, OH (US); Christoph Johann Schmitz, Euskirchen-Stotzheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 203 days.

(21) Appl. No.: 10/397,334

(22) Filed: Mar. 26, 2003

(65) Prior Publication Data

US 2004/0192140 A1    Sep. 30, 2004

(51) Int. Cl.[7] .......................... A61F 13/15; B32B 31/00
(52) U.S. Cl. ...................... 156/161; 156/160; 156/163; 156/164; 156/229
(58) Field of Search .............................. 156/160, 163, 156/164, 229, 161

(56) References Cited

U.S. PATENT DOCUMENTS

| | | |
|---|---|---|
| 3,468,748 A | 9/1969 | Bassett |
| 3,575,782 A | 4/1971 | Hansen |
| 4,720,415 A | 1/1988 | Vander Wielen et al. |
| 5,143,679 A * | 9/1992 | Weber et al. ............ 264/288.8 |
| 5,156,793 A | 10/1992 | Buell et al. |
| 5,167,897 A | 12/1992 | Weber et al. |
| 5,385,775 A | 1/1995 | Wright |
| 5,693,165 A | 12/1997 | Schmitz |
| 5,964,973 A * | 10/1999 | Heath et al. ............... 156/161 |
| 6,248,851 B1 | 6/2001 | Maugans et al. |

FOREIGN PATENT DOCUMENTS

| | | |
|---|---|---|
| EP | 330716 A2 * | 9/1989 |
| EP | 0 985 394 B1 | 9/2002 |
| WO | WO 01/87589 A2 | 11/2001 |
| WO | WO 01/88245 A2 | 11/2001 |

* cited by examiner

*Primary Examiner*—Jeff H. Aftergut
(74) *Attorney, Agent, or Firm*—Jay A. Krebs; Ken K. Patel (57) ABSTRACT

An elastomeric nonwoven laminate and a process for producing the elastomeric nonwoven laminate are proved. The elastomeric nonwoven laminate includes a first nonwoven, a second nonwoven and a plurality of elastic strands. The plurality of elastic strands is attached to the first nonwoven while under a strain producing a corrugated intermediate laminate once the strain is relieved. A second nonwoven is joined to the corrugated intermediate laminate and subsequently mechanically activated forming an elastomeric nonwoven laminate.

14 Claims, 6 Drawing Sheets

ELASTOMERIC NONWOVEN LAMINATES AND PROCESS FOR PRODUCING SAME

FIELD OF THE INVENTION

The present invention relates to a strand elastic and nonwoven layered material herein referred to as an elastomeric nonwoven laminate. The elastomeric nonwoven laminate may be used in a variety of articles and is particularly useful in disposable fluid-handling articles such as baby diapers, adult incontinence articles, feminine hygiene articles, baby swim diapers, dining bibs, wound dressings and any other articles where a cost effective stretchable material may be desirable. The present invention also relates to a method and apparatus for manufacturing the elastomeric nonwoven laminate.

BACKGROUND

Disposable fluid-handling articles are often produced on high-speed converting lines using continuous webs of fabrics, films, foams, elastics, etc. Many of these articles preferably include an elastic region or component. Typically this elastic component is covered on at least one side, and preferably two sides, by a nonwoven. This combination of nonwoven-elastic-nonwoven is referred to hereinafter as an elastomeric nonwoven laminate. The nonwoven portion of the laminate provides softness and opacity when the laminate is under tension so that the skin of a wearer is not visible through it during use. Opacity also provides an indication of the laminates structural integrity.

Elastomeric nonwoven laminates typically include elastic bonded to a nonwoven. The elastic may include elastic film or elastic strands. In one such laminate, a nonelastic nonwoven is joined to an elastic while the elastic is in a stretched condition so that when the elastic relaxes, the nonwoven gathers between the locations where it is bonded to the elastic forming corrugations. The resulting laminate is stretchable to the extent that the nonwoven gathered between the bond locations allows the elastic to elongate. The process is referred to as live stretch which is further defined herein. U.S. Pat No. 4,720,415 to Vander Wielen, et al., issued Jan. 19, 1988 discloses an example of this type of elastomeric laminate. Since the nonwoven portion of the elastomeric nonwoven laminate is not permanently deformed, the opacity characteristic of the material is not compromised. Therefore, the laminate provides good opacity in a relaxed state or under tension. However, additional nonwoven material is required to compensate for the corrugations.

Elastic strands for elastomeric nonwoven laminates are generally preferred over elastic films from both a cost and functional perspective since strands require less material and provide flexibility in arrangement and stretch properties. Elastic strands are typically attached to the nonwoven via an adhesive, which can often results in residual adhesive being exposed between the strands. The exposed adhesive can be problematic for downstream converting operations and for winding the elastomeric nonwoven onto rolls. In addition, exposed elastic strands fail to exhibit the softness and comfort desired by consumers. As a result, elastomeric nonwoven laminates often include two layers of nonwoven sandwiching the elastic strands. For such embodiments, the stretch properties of the elastomeric nonwoven laminate may be maintained by attaching the strands to both nonwoven layers simultaneously while under strain forming corrugations in both layers of nonwoven. The dual layers of corrugated nonwoven enhance the opacity characteristics of the laminate; however, further material is required to compensate for the corrugation effect in the second layer of nonwoven.

Another method of producing an elastomeric nonwoven laminate involves "zero strain" stretch laminate webs which comprise at least two plies of material secured to one another along at least a portion of their coextensive surfaces while in a substantially untensioned ("zero strain") condition. One of the plies employed in the "zero strain" stretch laminate is comprised of a material, which is stretchable and elastomeric, i.e., it will return substantially to its untensioned dimensions after an applied tensile force has been released. The second ply secured to the elastomeric ply is elongatable but not necessarily elastomeric. Upon stretching, the second ply will permanently elongate at least to a certain degree, so that upon release of the applied tensile forces, it will not fully return to its original undistorted configuration. The stretching is induced by mechanical activation which includes meshing the laminate between corrugated mating rolls as described in U.S. Pat. No. 5,143,679 issued to Weber, et al. Sep. 1, 1992; U.S. Pat. No. 5,156,793 issued to Buell Oct. 20, 1992; and U.S. Pat. No. 5,167,897 issued to Weber Dec. 1, 1992. Mechanical activation plastically deforms the nonelastomeric nonwoven material reducing the material thickness and creating thin spots in areas where meshing occurs. These thin spots exhibit less opacity, particularly when the laminate is under tension. However, since the nonwoven portion of the laminate is plastically deformed as opposed to being gathered which occurs with live stretch, less material is required in forming the elastomeric laminate.

Consequently, it would be beneficial to provide an elastomeric nonwoven laminate that uses less elastic, less nonwoven material, less adhesive, or any combination thereof, while having the desired elasticity, opaqueness, and softness desired by the consumer. In particular, it would be beneficial to provide such an elastomeric nonwoven material combining the advantages of live stretch with those of zero strain stretch laminates. It would also be beneficial to provide a method and apparatus for making such a material.

SUMMARY OF THE INVENTION

In order to solve one or more of the problems found in the art, an elastomeric nonwoven laminate and a method of producing the same is provided. An intermediate laminate is formed comprising a plurality of elastic strands attached to a first bonding surface of a first nonwoven while under a first strain ranging from about 20 percent to about 500 percent and extending in a machine direction of the first nonwoven. The plurality of elastic strands retracts once the strain is released forming corrugations in a first cross direction of the first nonwoven, which enable the intermediate laminate to be extensible in the first machine direction. A second nonwoven having a second machine direction, a second cross direction, and a second bonding surface is disposed in a face-to-face relationship with the first bonding surface of the first nonwoven. The second bonding surface of the second nonwoven is attached to at least a portion of the plurality of elastic strands while at least a portion of the strain on the plurality of elastic strands is relieved. The second nonwoven is mechanically activated making it extensible with the intermediate laminate. The second nonwoven is preferably disposed relative to the first nonwoven such that the second machine direction is perpendicular to the first machine direction and the second nonwoven is preferably mechanically activated in the second cross direction making it extensible in the second cross direction.

BRIEF DESCRIPTION SHOWN IN THE DRAWINGS

While the specification concludes with claims particularly pointing out and distinctly claiming the subject matter that is regarded as the present invention, it is believed that the invention will be more fully understood from the following description taken in conjunction with the accompanying drawings. None of the drawings are necessarily to scale.

DETAILED DESCRIPTION OF THE INVENTION

The method, material, and the apparatus of the present invention are designed to provide a more cost effective and/or consumer desirable elastomeric nonwoven laminate suitable for use in a variety of articles including a disposable fluid-handling article. The elastomeric nonwoven laminate comprises a nonwoven/elastic/nonwoven sandwich composed from at least one layer of corrugated nonwoven, a layer of elastic strands and a flat layer of nonwoven. When the laminate is mechanically activated, the flat layer of nonwoven is strained (plastically deformed) in the cross direction, while the elastic strands and the corrugated nonwoven are strained, but only to the extent that no plastic deformation occurs.

Definitions

The following terminology is used herein consistent with the plain meaning of the terms with further details provided in the present specification.

The term "activating" or activation refers to the process of making a nonwoven, or an elastic and nonwoven laminate more extensible.

"Live stretch" includes stretching elastic and bonding the stretched elastic to a nonwoven. After bonding the stretched elastic is released causing it to contract, resulting in a "corrugated" nonwoven. The corrugated nonwoven can stretch as the corrugated portion is pulled to about the point that the nonwoven reaches at least one original flat dimension. The elastic is preferably stretched at least 25% and more preferably at least 100% of its relaxed length when it is bonded to the nonwoven.

"Basis weight" refers to the weight of a planar material for a given surface area. Basis weight is typically measured in grams per square meter (gsm). The basis weight of an elastomeric laminate is typically measured in an unstrained configuration.

A "converting facility" refers to any production equipment producing one or more components of a disposable fluid-handling article that are subsequently assembled into a finished disposable fluid-handling article. It may also produce a finished disposable fluid-handling article that is complete for use by a consumer.

A "disposable fluid handling article" refers to an article device that normally absorbs and/or retains fluids. In certain instances, the phrase refers to articles that are placed against or in proximity to the body of the wearer to absorb and contain the excreta and/or exudates discharged from the body, and includes such personal care articles as baby diapers, baby training pants, adult incontinence articles, feminine hygiene articles, baby swim diapers, wound dressing, and the like. A disposable fluid-handling article is generally worn by infants and other incontinent persons about the lower torso.

The term "disposable" is used herein to describe products, which generally are not intended to be laundered or otherwise restored and reused for their original function. They are typically intended to be discarded after about 1 or 2 uses. It is preferred that such disposable articles be recycled, composted or otherwise disposed of in an environmentally compatible manner.

An "elastic," "elastomer" or "elastomeric" refers to polymers exhibiting elastic properties. They include any material that upon application of a force to its relaxed, initial length can stretch or elongate to an elongated length more than 10% greater than its initial length and will substantially recover back to about its initial length upon release of the applied force.

An "extrusion apparatus" or "extruder" refers herein to any machine capable of extruding a molten stream of material such as a polymeric through one or more extrusion dies.

The term "extrude" or "extruding" refers herein to a process by which a heated elastomer is forced through one or more extrusion dies to form a molten stream of elastic that cools into a solid.

The term "molten stream" refers herein to a linear deposit of a heated liquid material such as a polymeric exiting an extrusion apparatus. The stream may include continuous filaments, discontinuous fibers, or continuous films of a polymeric material. When cooled, the molten stream forms a strand elastic.

The term "joined" herein encompasses configurations whereby a material or component is secured directly or indirectly (by one or more intermediate members) to another material or component. An example of indirect joining is an adhesive. Direct bonding includes heat and or pressure bonding. Joining may include any means known in the art including, for example, adhesives, heat bonds, pressure bonds, ultrasonic bonds, and the like.

The term "nonwoven" refers herein to a material made from continuous (long) filaments (fibers) and/or discontinuous (short) filaments (fibers) by processes such as spunbonding, meltblowing, and the like. Nonwovens do not have a woven or knitted filament pattern.

Nonwovens are typically described as having a machine direction and a cross direction. The machine direction is the direction in which the nonwoven is manufactured. The cross direction is the direction perpendicular to the machine direction. Nonwovens are typically formed with a machine direction that corresponds to the long or rolled direction of fabrication. The machine direction is also the primary direction of fiber orientation in the nonwoven.

Figure 1A:
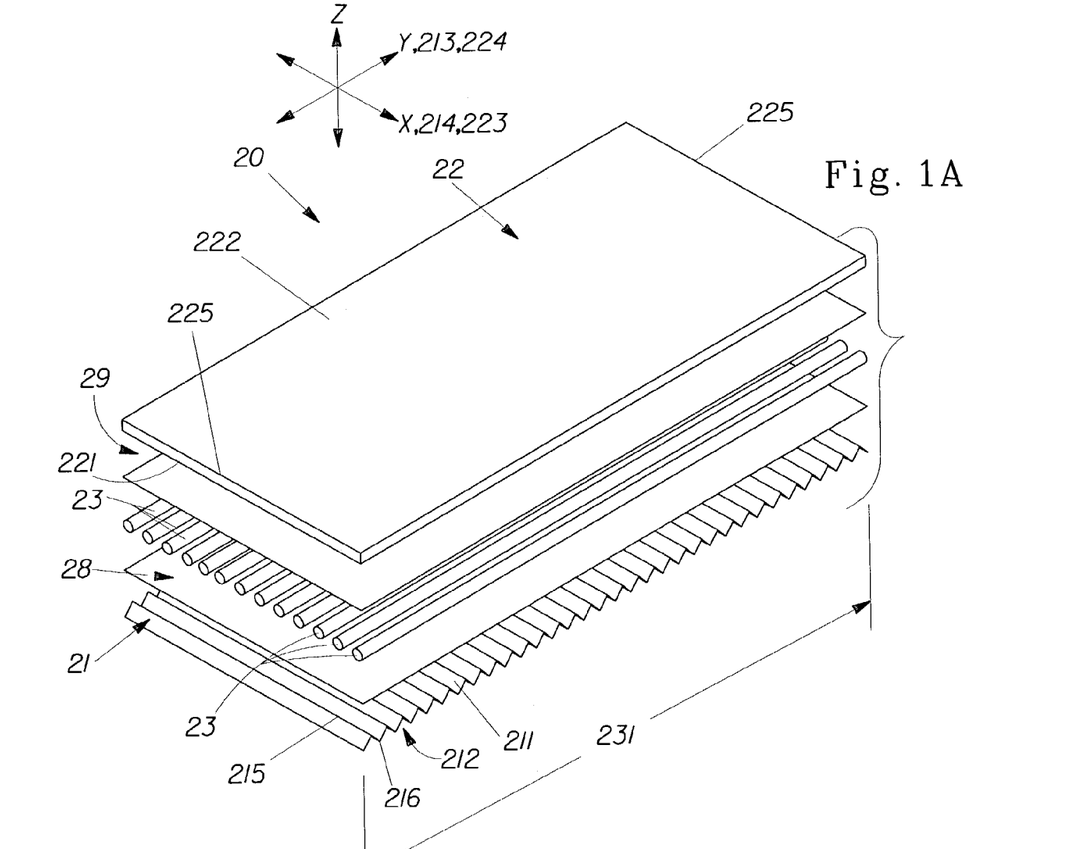
FIG. 1A is a three-dimensional exploded view of the elastomeric nonwoven laminate.

FIG. 1A shows a three-dimensional view of an elastomeric nonwoven laminate 20 according to the present invention in exploded view where the elements are separated to assist in describing the components. The laminate 20 includes a first nonwoven 21, a second nonwoven 22 and a plurality of elastic strands 23 having a strand elastic length 231. The first nonwoven 21 includes a first bonding surface 211 and a first exterior surface 212. The second nonwoven 22 includes a second bonding surface 221, a second exterior surface 222 and second opposite cross direction ends 225. An optional first adhesive 28 is located at least partially between the first bonding surface 211 and the is plurality of elastic strands 23. An optional second adhesive 29 is located at least partially between the second bonding surface 221 and the elastic strands 23. The first adhesive and/or second adhesive may be FINDLEY H 2031, or any other adhesive known in the art.

Figure 1B:
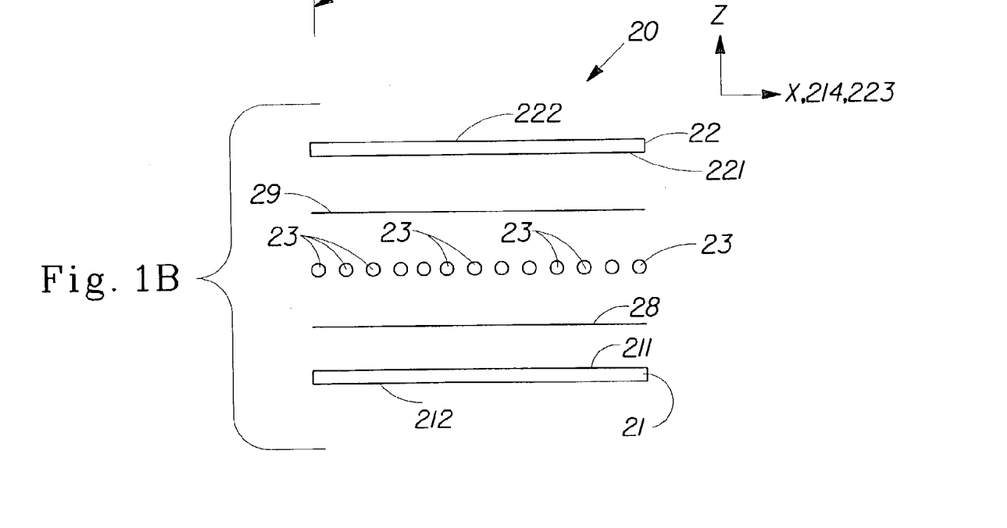
FIG. 1B is a cross-sectional exploded view of the elastomeric nonwoven laminate when viewed in the y-direction, looking at the zx-plane.
Figure 1C:
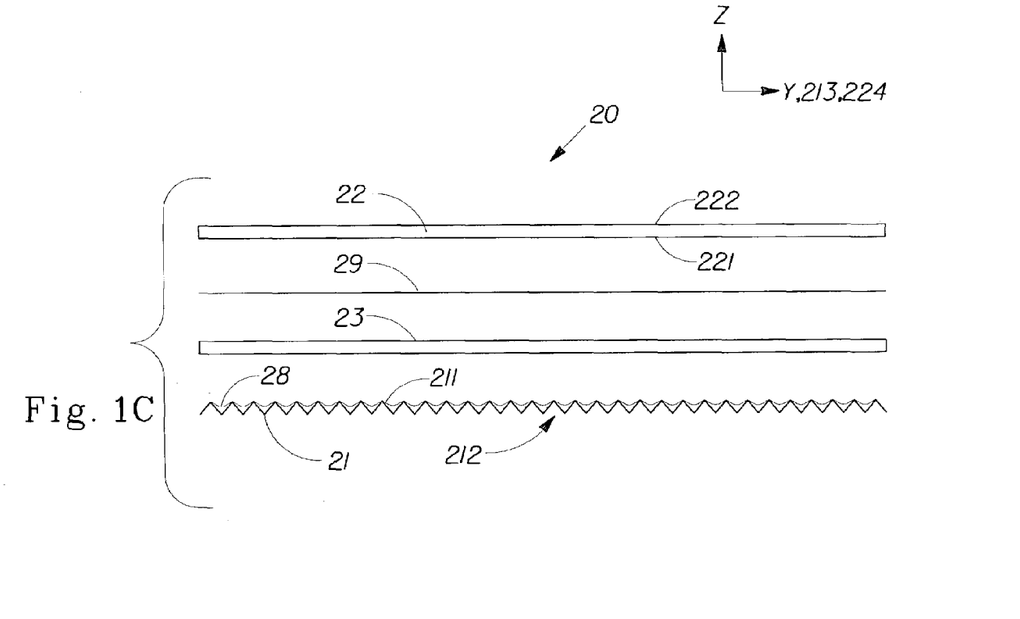
FIG. 1C is an alternate cross-sectional exploded view of the elastomeric nonwoven laminate when viewed in the x-direction, looking at the zy-plane.

FIG. 1A shows in an exaggerated form, a corrugation of the first nonwoven 21 with corrugation hills 215 and corrugation valleys 216 that occur after the first nonwoven is joined to the strand elastic 23. Corrugation is used to describe irregular corrugation hills 215 and corrugation valleys 216 that alternate. While FIGS. 1A, 1B, show the first adhesive 28 flat in relation to the corrugation of the second nonwoven 22, the first adhesive 28 is actually applied to the first bonding surface 211 prior to attachment of the elastic strands 23 while the first nonwoven 21 is in a flat configuration and the elastic strands are under strain. FIG. 1C, illustrates the actual corrugation of the first adhesive 28 and the first nonwoven 21 when bonded to the strand elastic 23 using live stretch.

As shown in FIG. 1A, the first nonwoven 21 is preferably corrugated in the first cross direction 214. When the corrugation hills 215 and corrugation valleys 216 alternate in about the first machine direction 213, the corrugation direction is in the direction in which the corrugation hills 215 and corrugation valleys 216 extend, or in the first cross direction 214. Once corrugated, the nonwoven and/or nonwoven elastic laminate is extensible perpendicular to the direction of corrugation. The amplitude of the corrugation is preferably less than 20 times the thickness of the un-corrugated nonwoven measured in the z-direction of FIG. 1A. The amplitude of the corrugation is more preferably less than 10 times the thickness of the un-corrugated nonwoven measured in the z-direction of FIG. 1A.

The first nonwoven may be corrugated using live stretch or mechanical activation, however, the corrugations are preferably formed using live stretch. As defined above, live stretch involves the process of bonding an elastic strand to a nonwoven while the elastic strand is under strain. The corrugations form in the nonwoven once the strain is relieved or else removed.

Strain is measured as the percent of length increase in the plurality of elastic strands under load. For example a strand with a free and stretchable strand length of 15 centimeters (cm) may have a load applied such that the 15 cm strand elastic is now 18 cm long. This length increase of 3 cm is 20% of 15 cm (3/15), or a 20% strain. The first strain may be from about 20% to about 500%, preferably from about 100% to about 400%, and more preferably from about 150% to about 300%.

As shown in FIG. 1A, the strained elastic strands 23 may be bonded with the first bonding surface 211, typically with a first adhesive 28. Once bonded, at least a portion of the first strain may be removed from the bonded portion of the first nonwoven 21 and plurality of elastic strands 23. As the strain is removed, the plurality of elastic strands contract back toward their original, pre strained length 231. This contraction causes the observed first nonwoven corrugation producing an extensible nonwoven. The bonded elastic strand 23 and first nonwoven 21 (prior to bonding with the second nonwoven) is herein referred to as an intermediate laminate.

As a result of the live stretch, the first nonwoven has an increased basis weight and opacity after corrugation because the elastic pulls the first nonwoven together in the first machine direction creating a shorter but denser nonwoven. The first nonwoven basis weight is increased upon corrugation in the range of from about 15% to about 400%, resulting in the corrugated first nonwoven having a corrugated basis weight in the range of about 12 gsm to about 100 gsm. Preferably, the corrugated basis weight of the first nonwoven is in the range of about 12 gsm to about 50 gsm.

As shown in FIG. 1A, the first nonwoven 21 has a first machine direction 213 corresponding to the y-axis direction and a first cross direction 214 corresponding to the x-axis direction. The second nonwoven 22 has a second machine direction 223 corresponding to the x-axis direction and a second cross direction 224 corresponding to the y-axis direction. The strand elastic length 231 extends in the first machine direction 213 and the second cross direction ends 225 are located opposite one another in the second cross direction 224.

The first nonwoven 21 and the second nonwoven 22 may be oriented relative to one another such that the first machine direction 213 of the first nonwoven 21 is about perpendicular to the second machine direction 223 of the second nonwoven 22 and about parallel to the strand elastic length 231. Since fibers are typically oriented in the machine direction, spaces between fibers provide see through lines, which may be visible even through laminates composed of nonwovens having parallel machine directions. Crossing the fiber directions by forming a laminate composed of nonwovens having perpendicular machine directions reduces the visibility through the laminate, thereby enhancing the opacity.

The perpendicular directions referenced are approximate and small variations ranging from about ±5 degrees to about ±15 degrees in the first nonwoven first machine direction 213 relative to the second nonwoven second machine direction 223 would not significantly impact the benefits associated with the orientation.

The second nonwoven is mechanically activated in the second cross direction after it is bonded to the elastic strands and/or first nonwoven (intermediate laminate) making the second nonwoven extensible in the second cross direction. Mechanical activation refers to a process wherein the nonwoven fibers are broken, and/or stretched, within the nonwoven so that the nonwoven is stretched in a direction along its surfaces and can be easily expanded in that direction by partial straightening of the fibers in the nonwoven.

When the second nonwoven is subject to the mechanical activation it typically has a localized decrease in density as it is "pulled" and stretched between adjacent ring roll teeth. The breaking and stretching of fibers can significantly decrease the basis weight of the nonwoven. In fact, the basis weight of the second nonwoven may decrease four fold or more as a result of mechanical activation. Since the first nonwoven is pulled together or corrugated as a result of the live stretch, mechanical activation has minimal affect on the density of the first nonwoven.

In one embodiment, the plurality of elastic strands attached to the first nonwoven may be subject to a second strain prior to being joined with the second nonwoven providing extensibility to the second nonwoven once the second strain is relieved. For this embodiment, the second strain is typically less than the first strain such that subsequent mechanical activation of the laminate results in deformation of the second nonwoven but not the first nonwoven. Alternatively, the second nonwoven may be mechanically activated prior to bonding with the elastic strands. For example, the second nonwoven may be mechanically activated and the second strain applied to the plurality of elastic strands as they are bonded to the mechanically activated second nonwoven.

The elastomeric nonwoven laminate of the present invention has several preferred performance characteristics, the combination of which may also be unique to the present invention. For instance, the elastomeric nonwoven laminate may have preferred combinations of opacity, extensibility and a force wall, which make it particularly desirable for use in disposable fluid-handling articles.

Opacity is the inhibition of light transmission through a material and often referred to as the see through nature of the material. The greater the opacity, the less light transmits through the material. Light transmission may be measured in accordance with ASTM-D2244-85 or the test procedure in WO 01/49230, Jordan et al., published Jul. 12, 2001.

The present invention is designed to improve the opacity of the elastomeric nonwoven laminate under strain. A higher opacity is desired because many consumers tend to equate opacity with thickness and quality. The filaments (fibers) in a nonwoven tend to be oriented in the machine direction with spacing between the fibers in the cross direction. Since light can transmit through the spacing between fibers in the cross direction, opacity of the nonwoven is increased by minimizing the spacing.

As previously explained, mechanical activation of the second nonwoven in the second cross direction stretches the second nonwoven in the second cross direction pulling the fibers oriented at least partially in the cross direction apart (breaking them) while increasing the spacing between the fibers oriented in the machine direction. As a result, the mechanical activation causes a decrease in density and opacity in the second nonwoven.

In contrast, live stretch causes the plurality of elastic strands to pull the first nonwoven together in the first machine direction forming a shorter but denser nonwoven with corrugations. As a result, the corrugated second nonwoven has an increase in density and opacity. Consequently, by joining the corrugated first nonwoven with the mechanically activated second nonwoven, the increase in opacity of the first nonwoven compensates for the reduced opacity experienced by the second nonwoven. Also, as previously described, orienting the first and second nonwovens with perpendicular machine directions can further enhance the opacity of the laminate.

Figure 2:
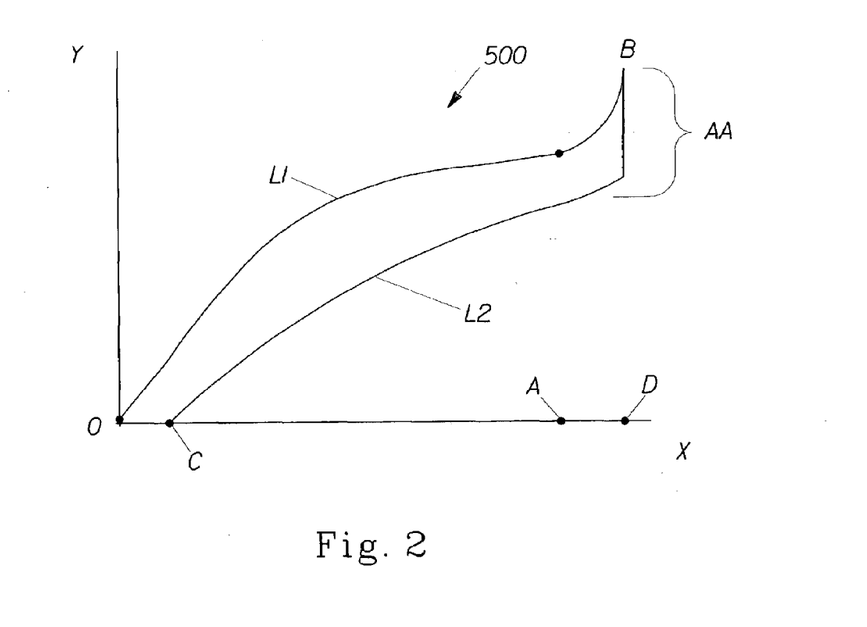
FIG. 2 is a sample hysteresis force vs. strain curve for an exemplary elastomeric nonwoven laminate with a force wall.

In addition to enhancing the opacity of the laminate, the corrugations produced in the first nonwoven provide a desired force wall in the elastomeric nonwoven laminate. FIG. 2 shows a hysteresis graph 500. The graph 500 has an x-axis and a y-axis. The x-axis is percent strain and the y-axis is force. When a force is applied to the elastomeric nonwoven laminate the resulting strain generally increases with increasing force until the strain reaches a force wall AA. As shown in FIG. 2, a force wall AA occurs in a region between point A and point D on the x-axis. The force wall AA occurs when the force required for a 10% increase in strain increases at least about 20%. A point B is the peak force applied during the force loading of the elastomeric nonwoven laminate. During the initial force loading, the force strain curve generally follows a first line L1 between a point O and a point B. During the removal of force, the force strain curve generally follows a second line L2 between point B and a point C. Once the force is removed, the elastomeric nonwoven laminate may not completely return to its original length. As a result, point C may or may not coincide with point O. The distance between a point O at the origin and the point C is referred to as the material set or simply "set." Preferably the maximum-targeted strain on the elastomeric nonwoven laminate during use would occur between a point A and a point D. When the elastomeric nonwoven laminate is loaded a second time, it may or may not follow the same curve created by the initial loading. Typically, less force will be required to achieve a given strain value in subsequent force loading cycles of the elastomeric nonwoven laminate.

The primary function of the elastomeric nonwoven laminate is to be stretchable. Preferably the elastomeric nonwoven laminate is capable of at least a 50% strain prior to reaching the force wall. Preferably, the elastomeric nonwoven laminate is capable of at least a 100% strain prior to reaching the force wall. More preferably, the elastomeric nonwoven laminate is capable of at least a 200% strain prior to reaching the force wall. Depending upon design choice and the particular application of the elastomeric nonwoven laminate, the force wall may be reached at a strain greater than 50%, 100%, 200%, or greater than 250%.

The first nonwoven 21 and the second nonwoven 22 may comprise any nonwoven material known in the art. The first nonwoven and the second nonwoven may comprise fibers made of polypropylene, polyethylene, polyester, nylon, cellulose, polyamide, or combinations of such materials. Fibers of one material or fibers of different materials or material combinations may be used in the first and/or second nonwoven.

Any process known in the art may be used to make the first nonwoven and/or the second nonwoven. Exemplary processes include spunbond, spunbond meltblown spunbond (SMS), spunbond meltblown spunbond (SMMS), carded and the like. Particularly acceptable nonwovens include high elongation carded (HEC) nonwovens and deep activation polypropylene (DAPP) nonwovens. While a meltblown nonwoven could be used as the second nonwoven, it is not preferred. Meltblown nonwovens do not mechanically activate as well as nonwovens made by other processes. However, a meltblown nonwoven may work well as the first nonwoven since the first nonwoven is not activated and uses live stretch.

The first nonwoven and the second nonwoven may comprise fibers that are bonded internally, including fibers that are needle punched, hydro entangled, spun bonded, thermally bonded, bonded by various types of chemical bonding such as laytex bonding, powder bonding, and the like. Preferably, the basis weight of the first nonwoven and/or second nonwoven is in the range of about 10 gsm to about 40 gsm. More preferably the basis weight of the first nonwoven is in the range of about 10 gsm to about 20 gsm and the basis weight of the second nonwoven is in the range of about 20 gsm to about 60 gsm.

The first nonwoven and/or the second nonwoven may comprise more than one layer of nonwoven material. For example the first nonwoven may include a nonwoven adhesively bonded to another nonwoven that is then bonded to the plurality of elastic strands. Similarly, the second nonwoven may include a nonwoven adhesively bonded to another nonwoven the combination of which is bonded to the intermediate laminate and subsequently activated.

The elastic strands 23 preferably extend in a generally parallel spaced relationship between the first nonwoven 21 and the second nonwoven 22. However, the elastic strands 23 may be arranged in any configuration desired. For instance, the strands may be arranged to provide a specific force profile in the elastomeric nonwoven laminate by varying the thickness of the individual strands or the spacing between them. Further, the elastic strands 23 may be skewed or oriented at an angle relative to the first and second machine directions of the first and second nonwovens providing an elastomeric nonwoven laminate having multidirectional stretch. For instance, the strands may be oriented and bonded between the first and second nonwovens and the second nonwoven may be subsequently mechanically activated in both the second machine direction and the second cross direction providing stretch properties in both the machine direction and the cross direction of the elastomeric nonwoven laminate.

In addition, the shape of the elastic strands is not limited. For example, typical elastic strands have a circular cross sectional shape, but sometimes the plurality of elastic strands may have different shapes, such as a trilobal shape, or a flat (i.e., "ribbon" like) shape. Further, the thickness or diameter of the elastic strands may vary in order to accommodate a particular application.

The plurality of elastic strands is preferably made of a resiliently elastic thermoplastic material. The elastic strands may be made from liquid elastic that is extruded through a die to achieve the desired strand elastic diameter and/or shape. The elastic strands are preferably styrene block copolymers, polyurethane or latex rubber having a diameter ranging between about 0.15 mm and about 0.5 mm and a density ranging from about 600 kg/m$^3$ to about 1250 kg/m$^3$.

The first nonwoven, second nonwoven and plurality of elastic strands may be joined by any joining means known in the art. Some examples of suitable joining means and/or methods for joining include, but are not limited to, adhesives, cohesives, thermal bonding, pressure bonding, mechanical bonds, ultrasonic bonding, and/or any combination of any known methods of joining such materials.

Figure 3:
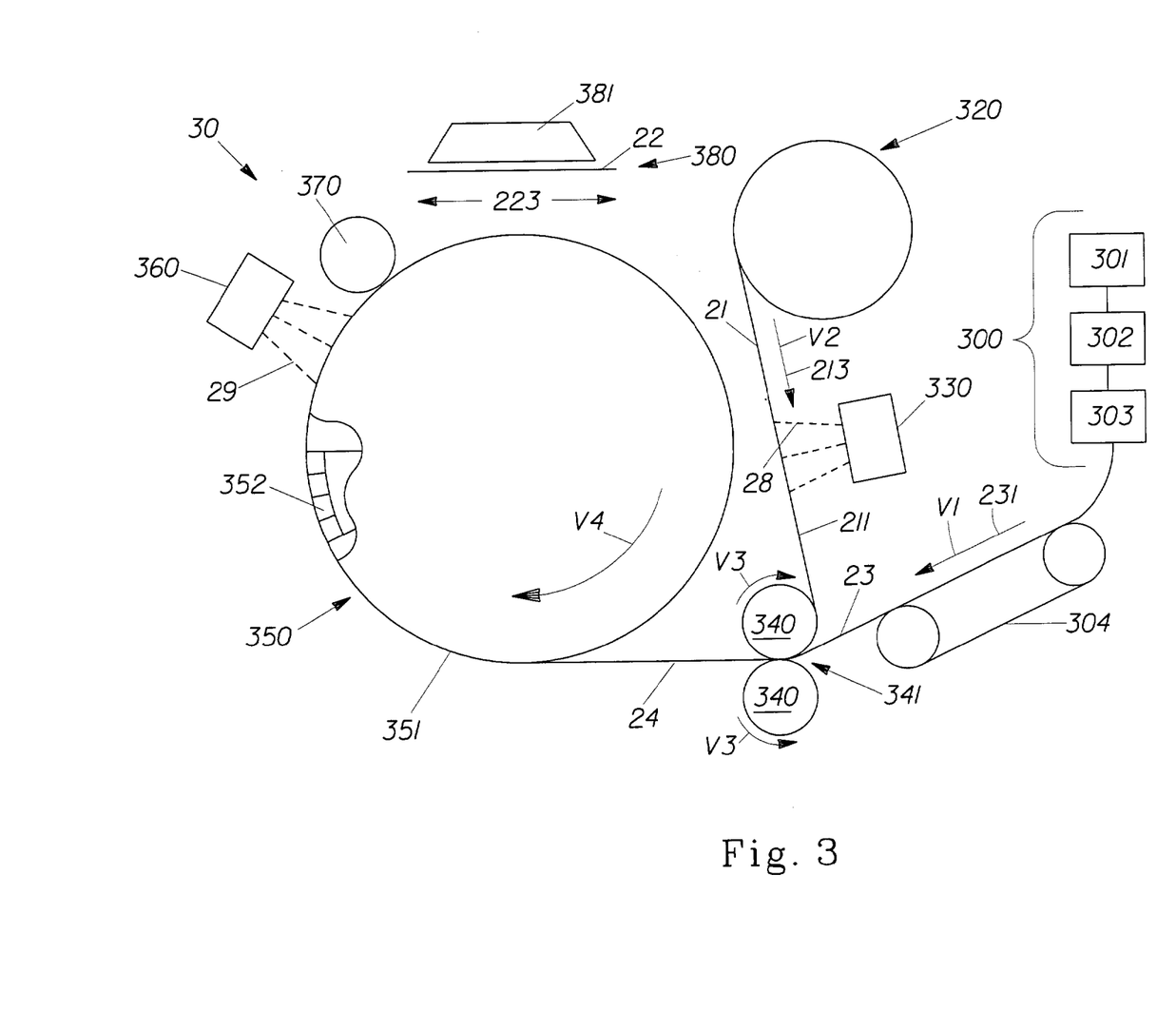
FIG. 3 is a simplified diagram of part of an on-line laminating apparatus for producing a nonwoven elastic laminate.

The elastomeric nonwoven laminate according to the present invention may be produced using the process and apparatus depicted in FIG. 3. As shown, the plurality of elastic strands 23 supplied by a strand elastic source 300 is conveyed via conveyor 304 at a first velocity V1 to a pair of rollers 340 rotating at a velocity V3. The strand elastic source 300 shown in FIG. 3 may include an extruder 301 that extrudes liquid elastic into an optional metering pump 302 and then into an extrusion die 303. The metering pump 302 measures and controls the flow of the elastic through temperature changes, process fluctuations, and the like. The strands of liquid elastic exit through the extruder die 303 onto the conveyer 304. The conveyer 304 is used to cool and solidify the plurality of elastic strands 23 prior to bonding with the first nonwoven 21. This method allows the diameter (or other cross section configuration) of the elastic strands 23 to be easily varied. The variation may be accomplished by changing the pressure in the extruder 301 and/or by changing the speed of the metering pump 302. In one embodiment, the extruder includes an extruder screw that operates at a speed. Changing the extruder screw speed and/or type can change the extruder pressure. Also, the extrusion die 303 can include a changeable die plate through which the strands of molten thermoplastic material are extruded. Alternatively, the strand elastic source 300 may be a prefabricated source of elastic strands such as a container of elastic strands (e.g. a box), or a roll of elastic strands.

A first nonwoven supplied from a source 320 is conveyed to the pair of rollers 340 at a second velocity V2. The first nonwoven source 320, shown in FIG. 3, may include a nonwoven continuous fabricator or a roll of prefabricated nonwoven. For example, the first nonwoven source 320 may be a prefabricated nonwoven on a roll arranged such that it is unwound as needed. Alternatively, the first nonwoven source 320 may comprise a continuous fabrication source using any suitable commercial hardware normally used in production of nonwovens.

A first adhesive is applied to the first bonding surface 211 of the first nonwoven 21 from an adhesive source located upstream of the nip 341 in the pair of rollers 340. The plurality of elastic strands 23 is fed from the conveyer 304 to the nip 341 at the first velocity V1. The first nonwoven 21 is fed from the first nonwoven source 320 to the nip 341 at the second velocity V2 such that the adhesive coated first bonding surface 211 contacts the plurality of elastic strands 23 joining them to the first nonwoven 21 and forming an intermediate laminate 24.

During operation of the apparatus 30 in FIG. 3, the first nonwoven second velocity V2 is greater than the plurality of elastic strands 23 first velocity V1. At the nip 341, a first strain is produced on the elastic strand 23 as a result of being extended in the first machine direction 213 due to the difference in velocity between the elastic strand first velocity V1 and the first nonwoven velocity V2. The pair of rollers 340 rotate producing a surface velocity V3 which is about equal to the second velocity V2. The greater the velocity differences between the first velocity V1 and the second velocity V2, the greater the resulting first strain. For the present invention, the difference in velocity creates a first strain on the plurality of elastic strands 23 ranging from about 20% to about 500%.

From the nip 341, the intermediate laminate 24 proceeds to an anvil drum 350. The anvil 350 is designed to have linear rotational velocity V4 and to hold the intermediate laminate 24 in place on the anvil surface 251. One means for holding the intermediate laminate 24 in place on the anvil drum surface 251 is by a partial anvil drum vacuum within the anvil drum 350. The anvil drum surface 251 may include an array of anvil perforations 352 providing a vacuum on the anvil drum surface 251 that pulls the first nonwoven 21 tight against the anvil drum surface 251. The anvil drum 350 may comprise one or several discrete parts and components. Each component may hold and release a local vacuum as needed during the manufacturing process.

The anvil drum 250 is capable of producing and maintaining a second strain on the plurality of elastic strands 23 of the intermediate laminate 24 even after the intermediate laminate 24 is cut by a first cutting means 370. The anvil drum vacuum prevents at least a portion of the first nonwoven from moving, which prevents the plurality of elastic strands from completely contracting to relieve the second strain. The second strain is determined by the difference between the first velocity V1, the third velocity V3 and the anvil velocity V4 as it rotates. It is also dependent upon the strength of the vacuum. The second strain is generally less than the first strain. The second strain is preferably from about 2 percent to about 150 percent.

Figure 4:
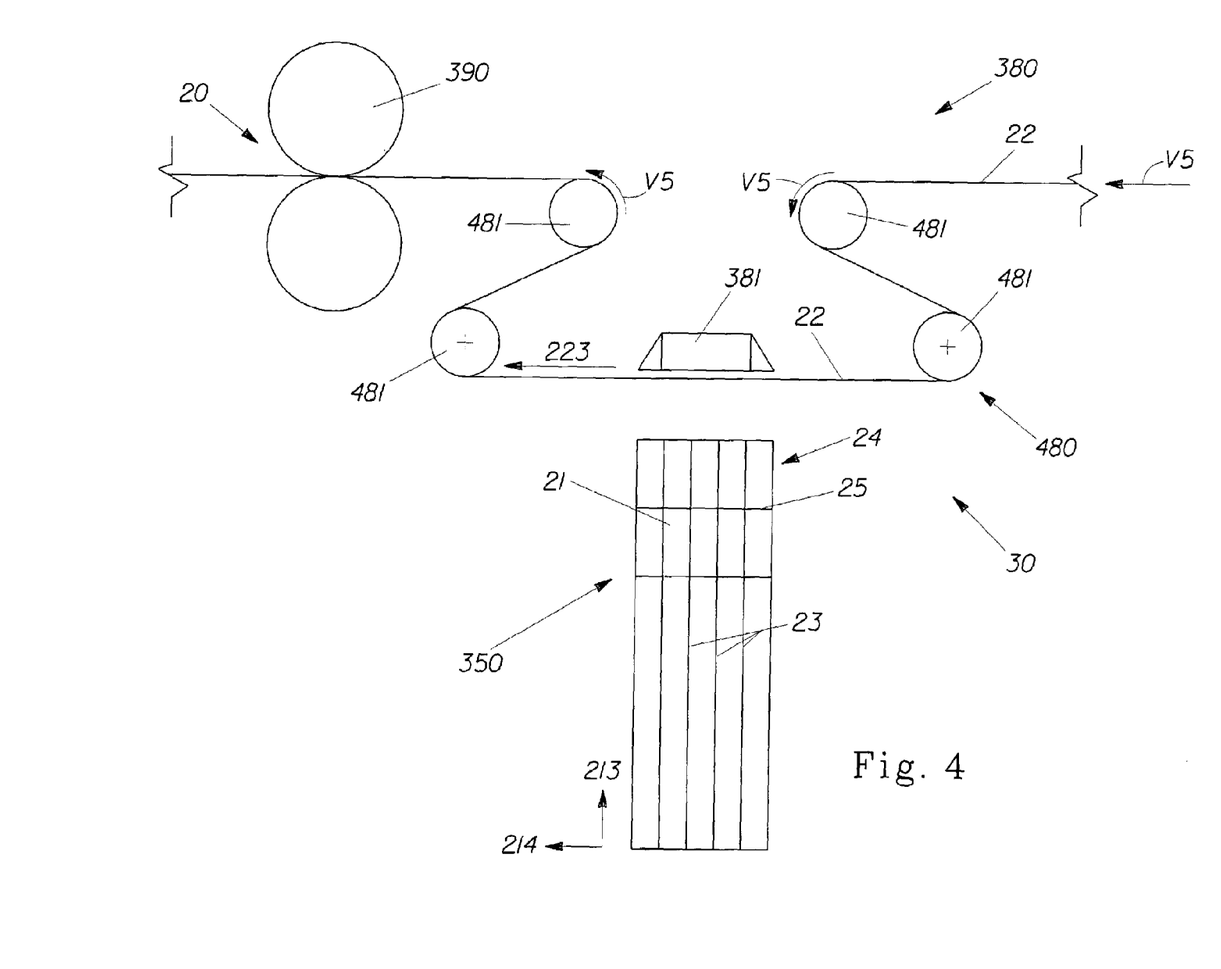
FIG. 4 is a simplified diagram of an alternate view of a part of the on-line laminating apparatus for producing a nonwoven elastic laminate.

A first cutter 370 slices the intermediate laminate 24 in about the first cross direction 214 at cuts 25 (shown in FIG. 4). The first cutter 370 may be any cutting means known in the art. Exemplary cutting means include a blade, ultrasonics, water jet, heat (melting), and the like.

An optional second adhesive 29 may be applied to the first bonding surface 211/elastic strands 23 forming the intermediate laminate 24 from a second adhesive source 360. The second adhesive applicator 360 is shown in FIG. 3 located prior to the first cutter 370, but the second adhesive applicator 360 may alternatively be located after the first cutter 370, but before the transfer press 381.

As shown in FIG. 3, a second nonwoven 22, supplied from a second nonwoven source 380, is conveyed in a second machine direction 223 to a transfer press 381 via a Festoon apparatus 480 described in Schmitz, U.S. Pat. No. 5,693,165, issued Dec. 2, 1997. The Festoon apparatus 480 is an arrangement of rollers 481 that have a rotational velocity and/or a translational velocity that allows a continuous nonwoven (e.g. the second nonwoven 22), traveling at a process velocity V5, to pause.

The intermediate laminate 24 is rotated into position under the transfer press 381 on the anvil drum 350. The transfer press 381 provides a means for joining the intermediate laminate 24 with the second nonwoven 22 and may be part of a converting facility. As shown in FIG. 4, the press 381 pushes the second nonwoven 22, paused by the Festoon apparatus 480, down onto the intermediate laminate 24 after it has been cut. When the press 381 rises away from the anvil, the cut piece of the intermediate laminate 24 is lifted off the anvil surface 251 with the second nonwoven 22 attached and proceeds to the mechanical activation source 390 shown in FIG. 4.

The mechanical activation source 390 may include any means known in the art including ring rolls or other meshed teeth arrangements. The mechanical activation may also be combined with ultrasonic activation as disclosed in Greer, U.S. patent application Ser. No. 09/854,009, filed May 11, 2001. In alternate embodiment, the second opposite cross direction ends 225 of the second nonwoven 22 are secured in place in order to prevent the second nonwoven 22 from being drawn into the mechanical activation source 390 in the second cross direction 224. This increases the strain on the second nonwoven in the second cross direction 224, resulting in greater extensibility of the nonwoven laminate 20 in the second cross direction 224. Further, in another embodiment the second nonwoven 22 may be mechanically activated by the mechanical activation means prior to being joined with the intermediate laminate 24, which would include prestraining the intermediate laminate 24 prior to bonding the activated second nonwoven 22.

Once the second nonwoven 22 is joined with the intermediate laminate 24, the second nonwoven 22 may be mechanically activated and then incorporated into an article such as the chassis of a disposable diaper. For instance, the elastomeric nonwoven laminate may be made to form an extendable side panel of the disposable diaper.

Alternatively, the second nonwoven 22 may be joined to the intermediate laminate 24 forming a nonwoven laminate, which is subsequently joined to a third nonwoven forming a nonwoven trilaminate wherein the exterior surface of the second nonwoven is joined to a bonding surface of the third nonwoven. The second and third nonwovens are mechanically activated forming an elastomeric nonwoven trilaminate. The third nonwoven may comprise a backsheet of an absorbent article such as a diaper wherein the addition of the intermediate laminate and subsequent mechanical activation of the second and third nonwovens produces an elastomeric nonwoven backsheet.

Figure 5:
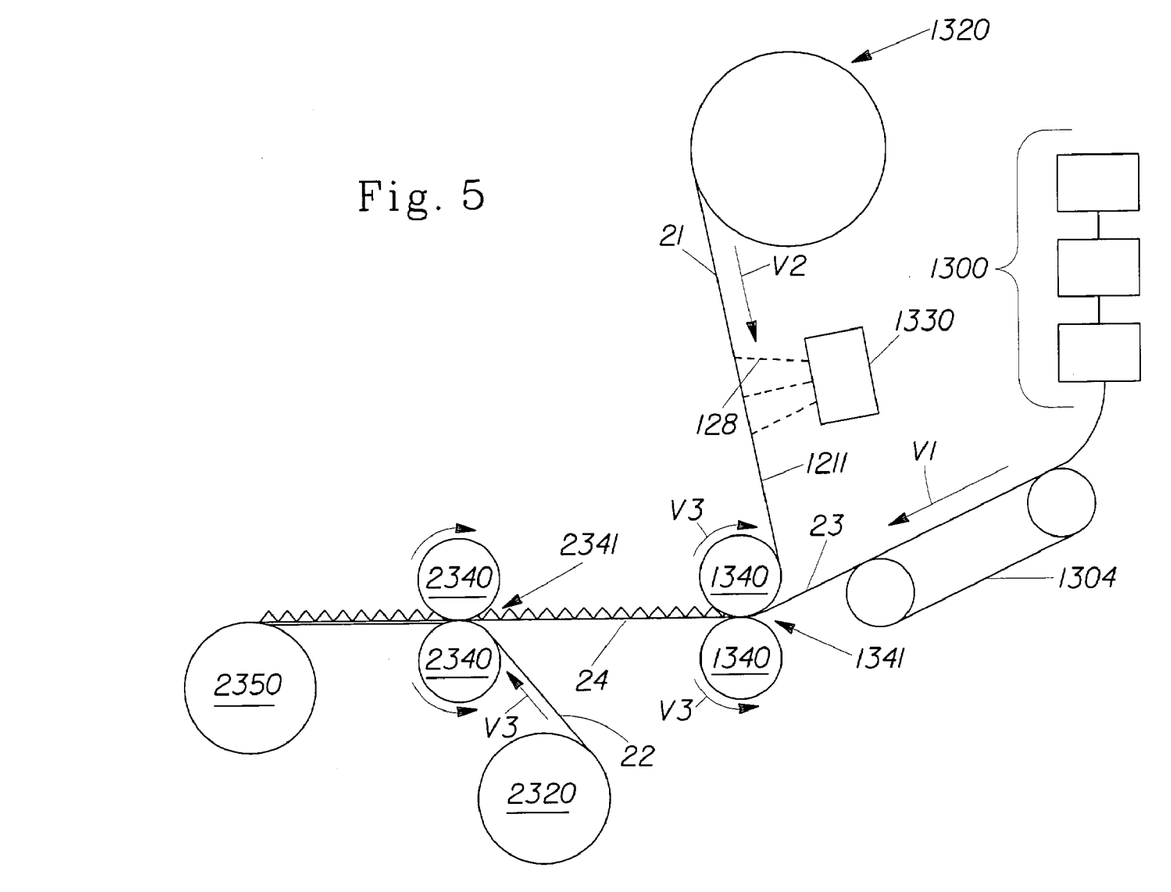
FIG. 5 is a simplified diagram of part of an on-line laminating apparatus for producing a nonwoven laminate, which is collected on a roll.

In an alternate process, the elastomeric nonwoven laminate may be collected on a roll and stored for future consumption. Such a process is illustrated in FIG. 5. As shown, plurality of elastic strands 23 supplied from strand elastic source 1300 is conveyed via conveyor 1304 at a first velocity V1 to a pair of rollers 1340 rotating and providing a surface velocity V3. A first nonwoven 21 supplied from a source 1320 is conveyed to the pair of rollers 1340 at a second velocity V2. The second velocity V2 is approximately equal to the third velocity V3, both of which are greater than the first velocity V1. A first adhesive 128 is applied to the first bonding surface 1211 of the first nonwoven 21 from an adhesive source 1330 located upstream of the nip 1341 in the pair of rollers 1340. The plurality of elastic strands 23 is fed from the conveyer 1304 to the nip 1341 at the first velocity V1. The first nonwoven 21 is fed from the first nonwoven source 1320 to the nip 1341 at the second velocity V2 such that the adhesive coated first bonding surface 1211 contacts the plurality of elastic strands 23 joining them to the first nonwoven 21 and forming an intermediate laminate 24. As a result of the difference in velocity between the first nonwoven 21 and the plurality of elastic strands 23, a first strain is placed on the plurality of elastic strands.

From the nip 1341, the intermediate laminate 24 proceeds to a second pair of rollers 2340 at a reduced velocity to enable the first strain placed on the plurality of elastic strands to at least partially relax forming corrugations in the intermediate laminate 24. A second nonwoven 22 supplied from a source 2320 is conveyed to the pair of rollers 2340 at a third velocity V3 that is slightly greater than the first velocity V1. Preferably, the third velocity V3 is 10% higher the first velocity V1. The intermediate laminate 24 and the second nonwoven 22 pass through nip 2341 joining the second nonwoven 22 to the intermediate laminate 24. Upon exiting the nip 2341, the laminate is nonelastomeric as a result of being restrained by the second nonwoven 22. The laminate is preferably collected on a roll in a nonelastomeric state in order to reduce creep experienced by the laminate during storage which can cause the elastomeric laminate to lose part of its elasticity. The laminate is later made elastomeric by mechanically activating the second nonwoven in a converting facility utilizing the laminate. Alternatively, the laminate can be made to proceed from nip 2341 to a mechanical activation source (not shown) in order to mechanically activate the second nonwoven 22 prior to collecting the laminate on roll 2350 for future use.

Figure 6:
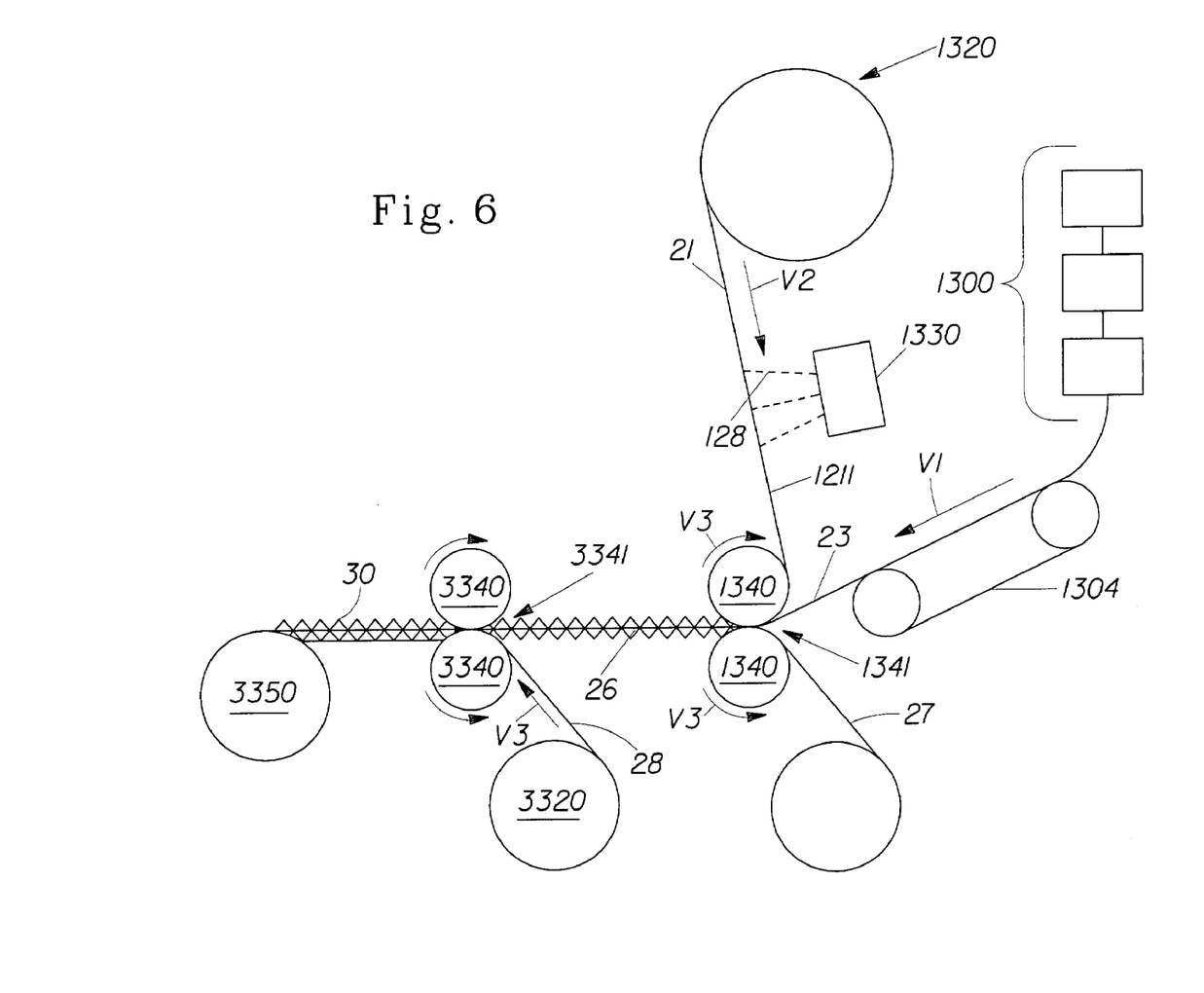
FIG. 6 is a simplified diagram of part of an on-line laminating apparatus for producing a nonwoven trilaminate, which is collected on a roll.

In another embodiment following a process shown in FIG. 6, which is similar to those previously described, the elastomeric nonwoven laminate includes three layers of nonwovens. For this embodiment, a first nonwoven 21 is joined with a second nonwoven 27 joined in a face-to-face relationship sandwiching a plurality of elastic strands 23 therebetween while the plurality of elastic strands are under a first strain. The first and second nonwoven 21, 27 and plurality of elastic strands 23 form a corrugated elastomeric laminate 26 once the first strain is relieved. The corrugated elastomeric laminate 26 passes through rollers 3340 where it is subsequently bonded to a third nonwoven 28 at nip 3341 forming trilaminate 30. The third nonwoven 28 of trilaminate 30 is eventually mechanically activated in a direction parallel to the plurality of elastic strands 23 providing an elastomeric nonwoven laminate.

As shown in FIG. 6, the trilaminate 30 is preferably collected on a roll 3350 prior to activating the third nonwoven to avoid creep. For this embodiment, the third nonwoven 28 is later mechanically activated as part of a converting operation in a converting facility.

Alternatively, the corrugated elastomeric laminate 26 may be collected on a roll for future use and later joined to the third nonwoven 28 as part of a converting operation. For instance, the third nonwoven 28 may form a portion of the backsheet of a disposable diaper which undergoes certain processing prior to being joined with the corrugated nonwoven. Once joined, the third nonwoven is mechanically activated to provide extensibility.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

All documents cited are, in relevant part, incorporated herein by reference; the citation of any document is not to be construed as an admission that it is prior art with respect to the present invention.

What is claimed is:

1. A method for manufacturing an elastomeric nonwoven laminate, the method comprising the steps of:
    a) providing a first nonwoven with a first bonding surface, a first machine direction and a first cross direction;
    b) providing a plurality of elastic strands, each strand having a strand elastic length;
    c) providing a first strain on the plurality of elastic strands along the strand elastic length of from about 20 percent to about 500 percent;
    d) placing the strained plurality of elastic strands upon the first bonding surface longitudinally with the strand elastic length about parallel to the first machine direction;
    e) joining at least a portion of the plurality of elastic strands to the first bonding surface to form a an intermediate laminate;
    f) relieving at least a portion of the first strain;
    g) providing a second nonwoven with a second bonding surface, a second machine direction, and a second cross direction;
    h) joining at least a portion of the plurality of elastic strands relieved of the first strain to the second bonding surface forming a nonwoven laminate; and
    i) mechanically activating at least the second nonwoven to provide an elastomeric nonwoven laminate.

2. The method of claim 1 wherein the elastomeric nonwoven laminate has a basis weight of less than 150 gsm and an elasticity of at least 50% before reaching a force wall.

3. The method of claim 1 further comprising the step of securing the intermediate laminate on an anvil drum, the anvil drum having an anvil surface with an array of anvil perforations wherein the intermediate laminate is held against the anvil surface by at least a partial vacuum through the anvil perforations.

4. The method of claim 3 further comprising the step of cutting the intermediate laminate in the first cross direction prior to joining at least a portion of the plurality of elastic strands to the second bonding surface of the second nonwoven.

5. The method of claim 4 wherein the second machine direction is about perpendicular to the first machine direction; and wherein the second nonwoven is mechanically activated in the second cross direction providing extensibility of the second nonwoven in the second cross direction.

6. The method of claim 5 wherein the second nonwoven includes second opposite cross direction ends, and the method further comprises the step of securing at least the second nonwoven at second opposite cross direction ends while activating the second nonwoven.

7. The method of claim 1 further comprising the step of providing a second strain on the intermediate laminate of from about 2 percent to about 500 percent prior to joining at least a portion of the plurality of elastic strands to the second bonding surface.

8. The method of claim 7 wherein the second strain is relieved from the plurality of elastic strands prior to the mechanical activation of the second nonwoven.

9. The method of claim 1 further comprising the step of collecting the second nonwoven on a roll prior to mechanically activating at least the second nonwoven.

10. A method for manufacturing an elastomeric nonwoven trilaminate, the method comprising the steps of:
    a) providing a first nonwoven with a first bonding surface and a first machine direction;
    b) providing a plurality of elastic strands, each strand having a strand elastic length;
    c) providing a second nonwoven with a second bonding surface and a second machine direction;
    d) providing a first strain on the plurality of elastic strands along the strand elastic length of from about 20 percent to about 500 percent;
    e) placing the strained plurality of elastic strands upon the first bonding surface of the first nonwoven and the second bonding surface of the second nonwoven longitudinally with the strand elastic length about parallel to the first machine direction and the second machine direction;
    f) joining at least a portion the plurality of elastic strands to the first bonding surface of the first nonwoven and the second bonding surface of the second nonwoven;
    g) relieving at least a portion of the first strain to form a corrugated elastomeric laminate;
    h) providing a third nonwoven with a third bonding surface;
    i) joining the corrugated elastomeric laminate to the third bonding surface of the third nonwoven forming a nonwoven trilaminate and
    j) mechanically activating the third nonwoven to make the nonwoven trilaminate elastomeric.

11. The method of claim 10 further comprising the step of collecting the nonwoven trilaminate on a roll prior to mechanically activating the third nonwoven.

12. A method for manufacturing an elastomeric nonwoven trilaminate, the method comprising the steps of:
    a) providing a first nonwoven with a first bonding surface and a first machine direction;
    b) providing a plurality of elastic strands, each strand having a strand elastic length;
    c) providing a first strain on the plurality of elastic stands along the strand elastic length of from about 20 percent to about 500 percent;
    d) placing the strained plurality of elastic stands upon the first bonding surface of the first nonwoven with the stand elastic length about parallel to the first machine direction;
    e) joining at least a portion the plurality of elastic strands to the first bonding surface of the first nonwoven to form an intermediate laminate;

f) relieving at least a portion of the first strain;
g) providing a second nonwoven with a second bonding surface and an exterior surface;
h) joining at least a portion of the plurality of elastic strands to the second bonding surface of the second nonwoven forming a nonwoven laminate;
i) providing a third nonwoven with a third bonding surface;
j) joining the third bonding surface of the third nonwoven to the exterior surface of the second nonwoven forming a nonwoven trilaminate and k) mechanically activating the second nonwoven and the third nonwoven to make the nonwoven trilaminate elastomeric.

13. The method of claim 12 further comprising the step of collecting the nonwoven laminate on a roll prior to joining the third nonwoven to the exterior surface of the second nonwoven.

14. The method of claim 12 wherein the third nonwoven forms the backsheet of a disposable absorbent article.

* * * * *